(12) United States Patent
Jeon et al.

(10) Patent No.: US 10,943,109 B2
(45) Date of Patent: Mar. 9, 2021

(54) ELECTRONIC APPARATUS, METHOD FOR CONTROLLING THEREOF AND THE COMPUTER READABLE RECORDING MEDIUM

(71) Applicants: Samsung Electronics Co., Ltd., Suwon-si (KR); Korea University Research and Business Foundation, Seoul (KR)

(72) Inventors: Kang-won Jeon, Seoul (KR); Sung-Jea Ko, Seoul (KR); Tae-young Na, Hanam-si (KR); Mun-Cheon Kang, Pohang-si (KR); Kwang-Hyun Uhm, Seoul (KR)

(73) Assignees: Samsung Electronics Co., Ltd., Suwon-si (KR); Korea University Research and Business Foundation, Seoul (KR)

( * ) Notice: Subject to any disclaimer, the term of this patent is extended or adjusted under 35 U.S.C. 154(b) by 149 days.

(21) Appl. No.: 16/122,095

(22) Filed: Sep. 5, 2018

(65) Prior Publication Data

US 2019/0073513 A1 Mar. 7, 2019

(30) Foreign Application Priority Data

Sep. 6, 2017 (KR) .......................... 10-2017-0113650

(51) Int. Cl.
*G06K 9/00* (2006.01)
*G01B 11/25* (2006.01)
(Continued)

(52) U.S. Cl.
CPC ........ *G06K 9/0061* (2013.01); *G01B 11/2513* (2013.01); *G06F 3/013* (2013.01);
(Continued)

(58) Field of Classification Search
CPC ............ G06K 9/0061; G06K 9/00604; G06K 9/00597; G01B 11/2513; G06F 3/013; A61B 3/0025; A61B 3/113
(Continued)

(56) References Cited

U.S. PATENT DOCUMENTS 6,101,007 A * 8/2000 Yamasaki ................ G03H 1/26
359/15
7,428,001 B2 * 9/2008 Schowengerdt ... G02B 27/0093
348/51
(Continued)

FOREIGN PATENT DOCUMENTS

JP 2012-257022 A 12/2012
JP 2016-100899 A 5/2016
KR 10-0947990 B1 3/2010

OTHER PUBLICATIONS

D. H. Yoo et al., "Non-contact eye gaze tracking system by mapping of corneal reflections," in Proc. 5th IEEE Int. Conf. Autom. Face Gesture Recog., pp. 94-99, 2002.

(Continued)

*Primary Examiner* — Marceau Milord
(74) *Attorney, Agent, or Firm* — Jefferson IP Law, LLP

(57) ABSTRACT

An electronic device is provided. The electronic device includes a light emitting unit configured to alternately emit light having a preset pattern to an eye area of a user; an inputter configured to receive a plurality of images which capture an eye area of the user; and a processor configured to detect a user's gaze using a first image that is captured at the time of irradiating a preset first pattern and a second image that is captured at the time of irradiating a preset second pattern, and the processor detects a user's gaze by extracting reflection points of each of the first image and the (Continued)

second image and using remaining reflection points excluding reflection points at a same position from among the extracted reflection points.

17 Claims, 11 Drawing Sheets

(51) Int. Cl.
*G06F 3/01* (2006.01)
*A61B 3/113* (2006.01)
*A61B 3/00* (2006.01)

(52) U.S. Cl.
CPC ..... *G06K 9/00597* (2013.01); *G06K 9/00604* (2013.01); *A61B 3/0025* (2013.01); *A61B 3/113* (2013.01)

(58) Field of Classification Search
USPC ................................ 382/117, 154, 288, 128
See application file for complete search history.

(56) References Cited

U.S. PATENT DOCUMENTS

| | | | | |
|---|---|---|---|---|
| 7,963,652 | B2* | 6/2011 | Vertegaal | G06T 7/73 351/205 |
| 8,964,298 | B2* | 2/2015 | Haddick | G06F 3/013 359/630 |
| 9,370,302 | B2* | 6/2016 | Krueger | A61B 3/113 |
| 9,485,487 | B2 | 11/2016 | Kroon | |
| 9,639,745 | B2 | 5/2017 | Williams et al. | |
| 9,788,714 | B2* | 10/2017 | Krueger | A61B 5/163 |
| 9,791,924 | B2* | 10/2017 | Shiu | G06F 1/163 |
| 9,830,513 | B2* | 11/2017 | Gustafsson | G02B 27/017 |
| 10,016,130 | B2* | 7/2018 | Ganesan | A61B 3/032 |
| 10,231,614 | B2* | 3/2019 | Krueger | G16H 50/20 |
| 10,430,985 | B2* | 10/2019 | Harrises | G02B 27/0172 |
| 10,565,446 | B2* | 2/2020 | Gustafsson | G02B 27/0093 |
| 10,674,912 | B1* | 6/2020 | Vaziri | G16H 40/67 |
| 2009/0284608 | A1 | 11/2009 | Hong et al. | |
| 2010/0253493 | A1* | 10/2010 | Szczerba | G08G 1/167 340/435 |
| 2012/0314933 | A1 | 12/2012 | Morifuji et al. | |
| 2014/0285429 | A1* | 9/2014 | Simmons | G02B 27/0172 345/156 |
| 2016/0085301 | A1* | 3/2016 | Lopez | G06F 3/013 345/156 |
| 2016/0150211 | A1 | 5/2016 | Hwang et al. | |
| 2016/0167672 | A1* | 6/2016 | Krueger | A61B 5/7282 340/576 |
| 2016/0187976 | A1 | 6/2016 | Levesque et al. | |
| 2016/0240012 | A1* | 8/2016 | Gruenler | B60R 1/00 |
| 2017/0036673 | A1* | 2/2017 | Lee | G06F 3/017 |
| 2017/0090562 | A1* | 3/2017 | Gustafsson | G06K 9/00604 |
| 2017/0090563 | A1* | 3/2017 | Gustafsson | G06F 3/04815 |
| 2017/0090564 | A1* | 3/2017 | Gustafsson | G06F 3/012 |
| 2017/0091549 | A1* | 3/2017 | Gustafsson | G06F 3/04815 |
| 2017/0123526 | A1 | 5/2017 | Trail et al. | |
| 2017/0188823 | A1* | 7/2017 | Ganesan | A61B 3/113 |
| 2017/0285337 | A1* | 10/2017 | Wilson | G02B 27/01 |
| 2017/0316264 | A1* | 11/2017 | Gustafsson | G02B 6/0008 |
| 2018/0225511 | A1* | 8/2018 | Gustafsson | G02B 27/0179 |
| 2018/0275409 | A1* | 9/2018 | Gao | G02B 27/0179 |
| 2018/0307905 | A1* | 10/2018 | Gustafsson | G06F 3/0485 |
| 2019/0371028 | A1* | 12/2019 | Harrises | G06T 11/60 |

OTHER PUBLICATIONS

C. Hennessey and P. Lawrence, "Improving the accuracy and reliability of remote system-calibration-free eye-gaze tracking," IEEE Trans. Biomedical Eng., vol. 56, No. 7, pp. 1891-1900, Jul. 2009.
Fukumoto et al. "Detection of Pupil and Corneal Reflection Using High-speed Camera for Gaze Detection Under Face Intense Illumination and a Solution of Glass Reflection Problem by Improving Light Source." International Conference on Human-Computer Interaction. pp. 475-480 (2015).
http://www.marketsandmarkets.com/Market-Reports/eye-tracking-market-144268378.html.
https://auto.v.daum.net/v/n1wnC90Hjd.
Y. Ma, S. Soatto, J. Kosecka, and S. Sastry, An invitation to 3D vision: From Images to Models, Springer, 2003, pp. 44-59.
D.H. Yoo and M.J. Chung, "A Novel Non-Intrusive Eye Gaze Estimation Using Cross-Ratio under Large Head Motion," Computer Vision and Image Understanding, vol. 98, No. 1, pp. 25-51, Apr. 2005.
E.D. Guestrin and M. Eizenman, "General Theory of Remote Gaze Estimation Using the Pupil Center and Corneal Reflections," IEEE Trans. Biomedical Eng., vol. 53, No. 6, pp. 1124-1133, Jun. 2006.
D. W. Hansen, L. Roholm, and I. G. Ferreiros, "Robust glint detection through homography normalization," in Proc. ACM Symp. Eye-Tracking Research and Applications, Safety Harbor, Florida, pp. 91-94 (2014).
https://techcrunch.com/2017/02/19/unlocking-the-potential-of-eye-tracking-technology/.
http://smarteye.se/technology/.
http://www.tobiipro.com/services/advertising/.
http://www.cio.com/article/2917194/wearable-technology/bmw-does-in-car-augmented-reality.html.
https://www.mercedes-benz.com/en/mercedes-benz/next/connectivity/the-new-human-machine-team/.
D. Li et al., "openEyes: a low-cost head-mounted eye-tracking solution," Proceedings of the 2006 symposium on Eye tracking research & applications. ACM. pp. 95-100, 2006.
F. Li et al., "Using structured illumination to enhance video-based eye tracking," In Proc. IEEE Int. Conf. on Image Processing, San Antonio, Texas, pp. 373-376 (2007).
R. Valenti and T. Gevers, "Accurate eye center location and tracking using isophote curvature," 2008 IEEE Conference on Computer Vision and Pattern Recognition, Anchorage, AK, 2008, pp. 1-8.
Fuhl et al., "Else: Ellipse selection for robust pupil detection in real-world environments," Proceedings of the Ninth Biennial ACM Symposium on eye tracking research & applications, pp. 123-130, 2016.
N. Yao and K.-K. Ma, "Adaptive Rood Pattern Search for Fast Block-Matching Motion Estimation," IEEE Trans. Image Process., vol. 11, No. 12, pp. 1442-1448. Dec. 2002.
J. Y. Bouguet, "Pyramidal implementation of the affine limas kanade feature tracker description of the algorithm," Intel Corporation, pp. 1-10, 2001.
F. Li et al., "A model-based approach to video-based eye tracking," Journal of Modern Optics, vol. 55, pp. 503-531, 2008.

* cited by examiner (a)　　　　　　　　　　(b)

(a)            (b)

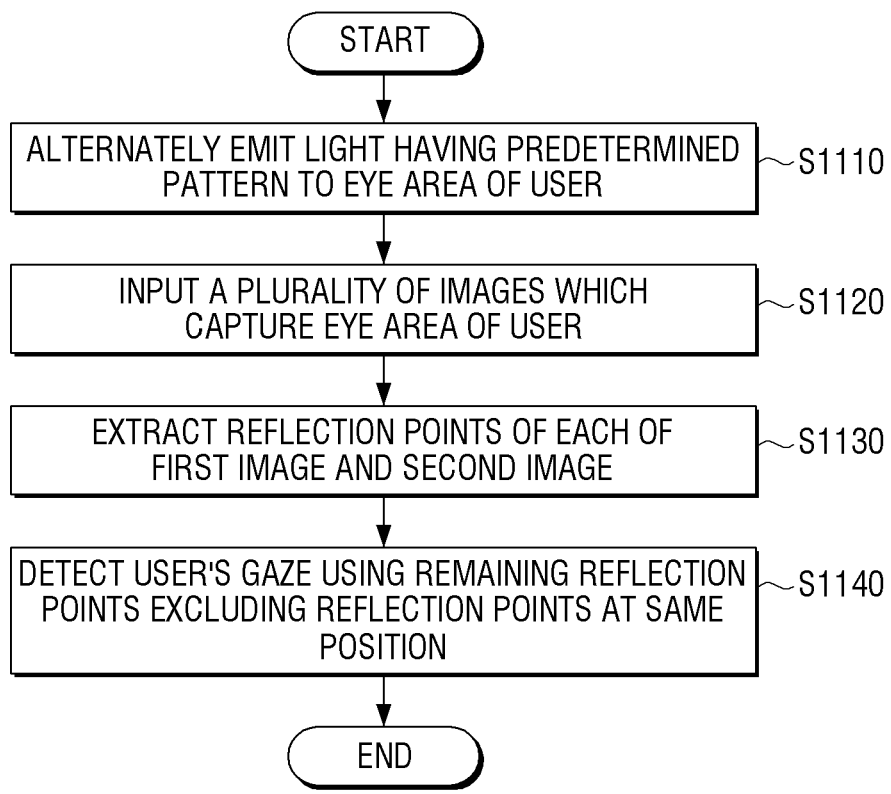

ELECTRONIC APPARATUS, METHOD FOR CONTROLLING THEREOF AND THE COMPUTER READABLE RECORDING MEDIUM

CROSS-REFERENCE TO RELATED APPLICATIONS

This application is based on and claims priority under 35 U.S.C. § 119 to Korean Patent Application No. 10-2017-0113650, filed in the Korean Intellectual Property Office on Sep. 6, 2017, the disclosure of which is incorporated by reference herein in its entirety.

BACKGROUND

1. Field

Aspects of the example embodiments relate generally to an electronic device, a control method thereof, and a computer readable recording medium and, more particularly, to an electronic device for detecting a user's gaze at outdoor environments, a control method thereof, and a computer readable recording medium.

2. Description of Related Art

Recently, there is a need for gaze tracking technology that is applicable to an outdoor environment as automobile, advertisement, marketing fields and so on require gaze tracking. In order to perform gaze tracking in an outdoor environment, it is most important to accurately detect the feature points of a user's eyes even under an external lighting environment. However, most of the conventional techniques are under the assumption of an indoor environment, and not many studies have been made regarding the feature point detection technique for the outdoor environment. Recently, adaptive techniques to the outdoor environment can be classified into a technique using a single image and a technique using a multi-image which captures user's eyes. However, the technique using a single image requires prior information on the feature points of the eye as well as prior information on the pattern of the infrared emitter, and the performance becomes unstable when the influence of external lighting is strong. In addition, the technique using multi-image requires complicated hardware such as requiring a high-speed camera.

Accordingly, there is a need for a technique for accurately detecting feature points of eyes in an outdoor environment using a low-cost general camera without prior knowledge of the pattern of an infrared radiator.

SUMMARY

An aspect of the example embodiments relates to an electronic device capable of accurately detecting feature points to detect a user's gaze even under various external lighting, a control method thereof, and a computer readable recording medium.

According to an exemplary embodiment, an electronic device includes a light emitting unit configured to alternately emit light having a preset pattern to an eye area of a user; an inputter configured to receive a plurality of images which capture an eye area of the user; and a processor configured to detect a user's gaze using a first image that is captured at the time of irradiating a preset first pattern and a second image that is captured at the time of irradiating a preset second pattern, and the processor detects a user's gaze by extracting reflection points of each of the first image and the second image and using remaining reflection points excluding reflection points at a same position from among the extracted reflection points.

The processor may generate a difference image on the first image and the second image, extract a reflection point from the generated difference image, and detect a user's gaze using the reflection point that is extracted from the difference image.

The processor may extract feature points respectively from the first image and the second image, and if positions of the extracted feature points are different, correct the second image so that the position of the feature point extracted from the second image is the same as the position of the feature point extracted from the first image.

The processor may, while the position of the feature point of the first image and the position of the feature point of the second image are coincided, extract a center point of a pupil in an eye area of a user from each of the first image and the second image, and if the positions of the extracted center points of the pupil are different, correct the second image to be coincided with the position of the extracted center point of the pupil of the first image.

The inputter may capture an eye area of the user at speed of 30 to 60 frames per second.

The light emitting unit may include a plurality of light emitting diode which are spaced apart from each other, and the processor may control the plurality of light emitting diode so that different light emitting diode emit light according to the first pattern and the second pattern.

The processor may control the plurality of light emitting diode so that all the plurality of light emitting diode emit light according to the first pattern and that all the plurality of light emitting diode not to emit light according to the second pattern.

The electronic device may further include a memory configured to store coordinate information on remaining reflection points excluding reflection points at a same position, from among the extracted reflection points, and the processor may detect a user's gaze by extracting a plurality of reflection points from a third image that is captured at the time of irradiating of a third pattern, from among the plurality of images, and using a reflection point selected based on the stored coordinate information from among the extracted plurality of reflection points.

The light emitting unit may include a plurality of light emitting diode which are spaced apart from each other, and the processor may control the plurality of light emitting diode so that all the plurality of light emitting diode emit light according to the third pattern.

A controlling method of an electronic device includes alternately emitting light having a preset pattern to an eye area of a user; receiving a plurality of images which capture an eye area of the user; and extracting reflection points of each of a first image that is captured at the time of irradiating a preset first pattern and a second image that is captured at the time of irradiating a preset second pattern; and detecting a user's gaze by extracting reflection points of each of the first image and the second image and using remaining reflection points excluding reflection points at a same position from among the extracted reflection points.

The detecting may include generating a difference image on the first image and the second image, extracting a reflection point from the generated difference image, and detecting a user's gaze using the reflection point that is extracted from the difference image.

The method may further include extracting feature points respectively from the first image and the second image; and if positions of the extracted feature points are different, correcting the second image so that the position of the feature point extracted from the second image is the same as the position of the feature point extracted from the first image.

The method may further include, while the position of the feature point of the first image and the position of the feature point of the second image are coincided, extracting a center point of a pupil in an eye area of a user from each of the first image and the second image; and if the positions of the extracted center points of the pupil are different, correcting the second image to be coincided with the position of the extracted center point of the pupil of the first image.

The inputting may include capturing an eye area of the user at speed of 30 to 60 frames per second.

The emitting may include emitting different light emitting diode from among a plurality of light emitting diode which are spaced apart from each other according to the first pattern and the second pattern.

The emitting may include emitting the plurality of light emitting diode according to the first pattern and not emitting the plurality of light emitting diode according to the second pattern.

The method may further include storing coordinate information on remaining reflection points excluding reflection points at a same position, from among the extracted reflection points; extracting a plurality of reflection points from a third image that is captured at the time of irradiating of a third pattern from among the plurality of images; and detecting a user's gaze using reflection points that are selected based on the stored coordinate information from among the extracted plurality of reflection points.

The emitting may include emitting all the plurality of light emitting diode that are spaced apart from each other according to the first pattern and the second pattern.

According to an exemplary embodiment, a computer readable recording medium including a program for executing a control method of an electronic device, wherein the control method may include alternately emitting light having a preset pattern to an eye area of a user; receiving a plurality of images which capture an eye area of the user; and extracting reflection points of each of a first image that is captured at the time of irradiating a preset first pattern and a second image that is captured at the time of irradiating a preset second pattern; and detecting a user's gaze by extracting reflection points of each of the first image and the second image and using remaining reflection points excluding reflection points at a same position from among the extracted reflection points.

BRIEF DESCRIPTION OF THE DRAWINGS

The above and/or other aspects of the present disclosure will be more apparent from the following detailed description, taken in conjunction with the accompanying drawings, in which like reference numerals refer to like elements, and wherein:

FIG. 11 is a flowchart to describe a method of detecting a user's gaze according to an exemplary embodiment.

DETAILED DESCRIPTION

Figure 1:
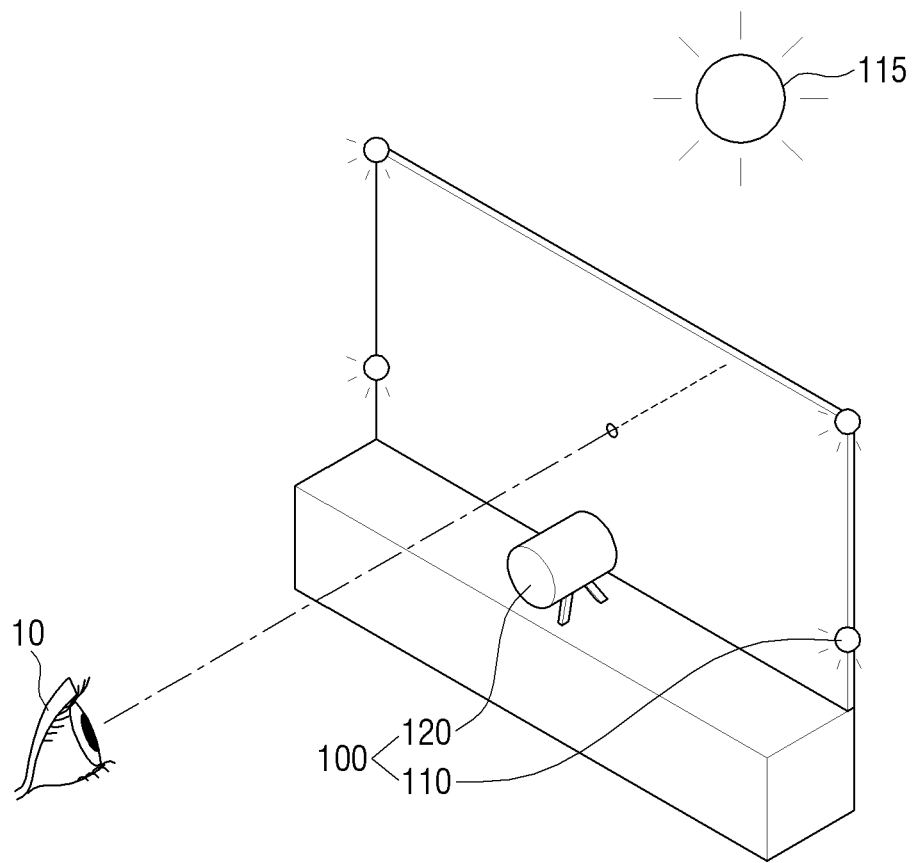
FIG. 1 is a view to describe a method of detecting a user's gaze in an outdoor environment according to an exemplary embodiment.

Certain example embodiments are described in greater detail below with reference to the accompanying drawings.

The terms used in the embodiments of the present disclosure are general terms which are widely used now and selected considering the functions of the present disclosure. However, the terms may vary depending on the intention of a person skilled in the art, a precedent, or the advent of new technology. In addition, in a special case, terms selected by the applicant may be used. In this case, the meaning of the terms will be explained in detail in the corresponding detailed descriptions. Accordingly, defining the terms used herein will be based on the meanings of the terms and overall contents of exemplary embodiments, rather than simple names of the terms.

As embodiments may have a variety of modifications and several examples, certain embodiments will be exemplified in the drawings and described in detail in the description thereof. However, this does not necessarily limit the scope of the embodiments to a specific embodiment form. Instead, modifications, equivalents and replacements included in the disclosed concept and technical scope of this specification may be employed. While describing embodiments, if it is determined that the specific description regarding a known technology obscures the gist of the disclosure, the specific description is omitted.

In the present disclosure, relational terms such as first and second, and the like, may be used to distinguish one entity from another entity, without necessarily implying any actual relationship or order between such entities. In embodiments of the present disclosure, relational terms such as first and second, and the like, may be used to distinguish one entity from another entity, without necessarily implying any actual relationship or order between such entities.

It is to be understood that the singular forms "a," "an," and "the" include plural referents unless the context clearly dictates otherwise. The terms "include", "comprise", "is configured to," etc., of the description are used to indicate that there are features, numbers, steps, operations, elements, parts or combination thereof, and they should not exclude the possibilities of combination or addition of one or more features, numbers, steps, operations, elements, parts or a combination thereof.

According to embodiments, a "module" or "unit" performs at least one function or operation, and may be implemented as hardware or software, or a combination of hardware and software. In addition, a plurality of 'modules' or a plurality of 'units' may be integrated into at least one module and may be realized as at least one processor except for 'modules' or 'units' that should be realized in a specific hardware.

Hereinbelow, certain embodiments will now be described in greater detail with reference to the accompanying drawings to enable those skilled in the art to work the same with ease. However, embodiments may be realized in a variety of different configurations, and not limited to descriptions provided herein. Further, those that are irrelevant with the description are omitted so as to describe embodiments more clearly, and similar drawing reference numerals are used for the similar elements throughout the description.

Hereinbelow, the present disclosure will be further described with reference to drawings.

FIG. 1 is a view to describe a method of detecting a user's gaze in an outdoor environment according to an exemplary embodiment.

Referring to FIG. 1, an electronic device 100 may track a gaze of a user 10 using a light emitting unit 110 and an inputter 120. To be specific, the electronic device 100 may make the light emitting unit 110 including a plurality of light-emitting elements emit light. Then, the electronic device 100 may receive an image which captures a reflection point that is a point that light is reflected from among an eye area of the user 10 through the inputter 120 and track a gaze of the user 10 using the input image. Herein, the inputter 120 may be a capturing unit such as an infrared camera which captures eyes of the user 10.

In the outdoor, external light 115 other than the light emitting unit 110 exists. Here, the external light 115 may include sun light, street light, and the like. Accordingly, the eye image of the user 10 input through the inputter 120 may include a reflection point of the external light 115 other than the light emitting unit 110.

In this case, the electronic device 100 uses the remaining points except the reflection points of the external light 115 among the plurality of reflection points included in the eye image of the user 10 input through the inputter 120 to tract the gaze of the user 10. This will be described below in detail with reference to FIGS. 2 to 11.

Figure 2:
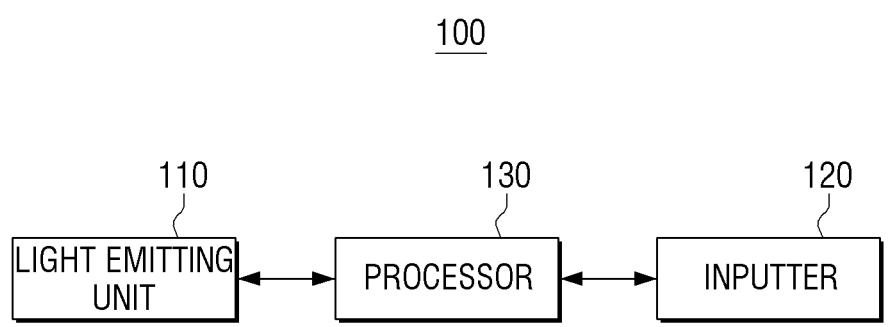
FIG. 2 is a block diagram to describe a brief configuration of an electronic device according to an exemplary embodiment.

FIG. 2 is a block diagram to describe a brief configuration of an electronic device according to an exemplary embodiment.

Referring to FIG. 2, the electronic device 100 includes the light emitting unit 110, the inputter 120, and a processor 130.

The light emitting unit 110 alternately irradiates light having a preset pattern. Specifically, the light emitting unit 110 includes a plurality of light emitting diode spaced apart from each other for irradiating light to a user's eye area, and different light emitting diode may emit light according to a preset pattern under the control of the processor 130.

For example, if the light emitting unit 110 includes four light emitting devices arranged in a rectangular shape and is referred to as light emitting diode 1, 2, 3, 4 in the clockwise direction from the upper left light emitting element, the second pattern in which the light emitting diode 3 and 4 emit light can be repeated after the first pattern in which the light emitting diode 1 and 2 emit light according to a preset pattern. Here, the light emitting element that emits light according to the first pattern and the light emitting element that emits light according to the second pattern may be different light emitting diode. In the meantime, the light emitting element includes an LED such as an incandescent light, an infrared ray light, an LED light and the like, and the type and the number thereof are irrelevant.

Meanwhile, the light emitting unit 110 can change the pattern at a preset speed under the control of the processor 130 and irradiate light. Here, the preset speed may correspond to the photographing speed of the image sensing unit which photographs the eye area of a user. However, the present disclosure is not limited thereto, and the light emitting unit 110 may change the pattern at a slower or faster speed than the photographing speed of the image capturing unit.

The inputter 120 receives a plurality of images of a user's eye area. Here, the plurality of received images may include reflection points by the light emitting unit 110 and external lighting. Specifically, the inputter 120 may include a capturing unit for imaging the user's eye area. Here, the inputter 120 includes a general camera using a visible ray, an infrared camera, and the like, and the kind thereof is irrelevant. In this case, the inputter 120 may include a camera for photographing at a speed of 20 to 60 frames per second in addition to a high-speed camera for photographing at a speed of 2000 frames per second.

In the meantime, when the electronic device 100 does not include an image capturing unit, the inputter 120 may include a communication unit that receives a plurality of images of an eye area of the user from an external device. Here, the external device may be an apparatus having an image capturing unit for photographing the eye area of the user.

The processor 130 may first control the light emitting unit 110 to alternately emit light in a preset pattern. Here, the light emitting unit 110 may include a plurality of light emitting devices, and the processor 130 may control the light emitting unit 110 such that light forming each pattern is irradiated by different light emitting diode.

The processor 130 can detect the user's gaze using the plurality of images input by the inputter 120. Here, the processor 130 can detect the user's gaze using the first image captured at the irradiation point of the preset first pattern and the second image captured at the irradiation point of the second pattern among the plurality of input images. Here, the first image and the second image may be consecutive frames. The first pattern and the second pattern may be formed by emitting light from different light emitting diode among a plurality of light emitting diode constituting the light emitting unit 110. Accordingly, the user's eye area of the first image and the second image may include reflection points of different patterns.

Specifically, the processor 130 may extract the reflection points of each of the first image and the second image, and use the remaining reflection points excluding the reflection points contained in the same positions of the first image and the second image among the extracted reflection points to detect user's gaze.

Specifically, the processor 130 may generate a difference image of the first image and the second image, and extract a reflection point from the generated difference image. Here, the first pattern and the second pattern may be displayed on the difference images of the first image and the second image because the first and second patterns are different from each other. Here, since the reflection points by the external lighting are displayed at the same positions of the first image and the second image, the reflection points can be removed in the difference images of the first image and the second image. Accordingly, in the reflection points extracted from the difference images of the first image and the second image by the processor 130, the reflection points by external lighting are removed, and the processor 130 can use all the reflection points extracted from the difference images to detect the user's gaze.

The processor 130 may extract the reflection points in each of the first image and the second image. Specifically, since the reflection point due to light will have the greatest brightness, the processor 130 can extract a point having a high brightness as a reflection point. The processor 130 may use the coordinates of the reflection points extracted from the first image and the second image to detect the user's line of sight by excluding the reflection points having the same coordinates and using the remaining reflection points. As described above, since the reflection points of different patterns are included in each image, it is possible to eliminate the reflection points due to external lighting and precisely detect the user's gaze without providing prior information on the position of the light emitted from the light emitting unit 110.

When there is a position change of the user between photographing of the first image and the second image, the processor 130 corrects position change to extract reflection points that are required to detect the user's gaze.

Specifically, the processor 130 can extract feature points from the first image photographed at the time of irradiating the light of the first pattern and the second image photographed at the time of irradiating the light of the second pattern. Here, the feature point may be separated from the reflection points included in the eye area of the user. For example, it may be a starting point or a tail point of the user's eye, or a point area included in an area other than the eye area among the user's face area, which is a characteristic that the structure does not change even if the position of the user's face moves. Here, if only the position of the face of the user is moved and the position of the eye is not moved, the processor 130 may extract the center point of the pupil as a feature point.

When the first pattern is formed by not emitting all of the plurality of light emitting diode and the second pattern is formed by emitting all the plurality of light emitting diode of the light emitting unit 110, the first image photographed at the time of irradiation of light in the first pattern may include reflection points due to external lighting. In addition, even if the position of the user's face moves, the position shift of the reflection point due to the inter-frame external lighting will not be great. Accordingly, the processor 130 may extract the reflection points due to the external lighting included in the first image as feature points, and the reflection points at positions closest to the feature points extracted from the first image, from among the plurality of reflection points included in the second image, as the feature points.

The processor 130, if the position of the feature point extracted from the first image is different from the position of the feature point extracted from the second image, may correct the second image so that the feature point of the second image is coincided with the feature point of the first image. Specifically, the processor 130 can move the position of the entire second image such that the feature points extracted from the second image are located at positions of the feature points extracted from the first image.

In addition, when the direction of the gaze as well as the position of the user's face between the first image and the second image is changed, the processor 130 may correct the position of the face and the direction of the gaze to extract a reflection point necessary for detecting the gaze.

Specifically, through the above-described correction, in a state where the positional shift of the user's face is corrected, the processor 130 can extract the center point of the pupil in the eye area of the user of the first image and the second image. Here, since the center point of the pupil is the lowest brightness area, the processor 130 can extract the area having the lowest brightness in the image as the center point of the pupil.

Specifically, the processor 130 may extract the center point of the pupil in the first image and the second image with the positions of the feature points of the first image and the second image matched, and if the center points of the extracted pupils are different, the processor may correct the second image so that the center point of the second image coincides with the position of the center point of the pupil extracted from the first image. Specifically, the processor 130 can correct the second image such that the center point of the pupil extracted from the second image is located at the position of the center point of the pupil extracted from the first image. At this time, the processor 130 may use an optical relationship between the center point of the pupil and the reflection point for compensating for eye movement. Specifically, since there is a constant ratio between the center point of the pupil and the change of the position of the reflection point when the eye rotates, the processor 130 can correct the positional change of the reflection point using the change in the position of the center point of the pupil.

Such a correction operation may be performed based on extracted feature points by extracting the feature points, after extracting all the reflection points of the first image and the second image. In the meantime, the feature points may be extracted and corrected before extracting the reflection points in each image, and then the reflection points may be extracted from the first image and the corrected second image, respectively. Then, the processor 130 can detect the user's gaze using the corrected reflection point.

The processor 130 can track the movement of the user's gaze while repeatedly performing the gaze detection. In addition, the processor 130 may perform an event corresponding to the detected user's gaze or the gaze movement of the tracked user. For example, the processor 130 may place a cursor at a position viewed by the user through the gaze detection of the user, and may perform an operation of moving the cursor according to the movement of the user's gaze.

As described above, by using two images including reflection points for light having different patterns, it is possible to grasp the pattern of the light emitting unit without prior knowledge of the pattern of the light emitting unit, and it is possible to detect the reflect point to detect the user's gaze more correctly using a low-cost general camera even in an outdoor environment.

Figure 3:
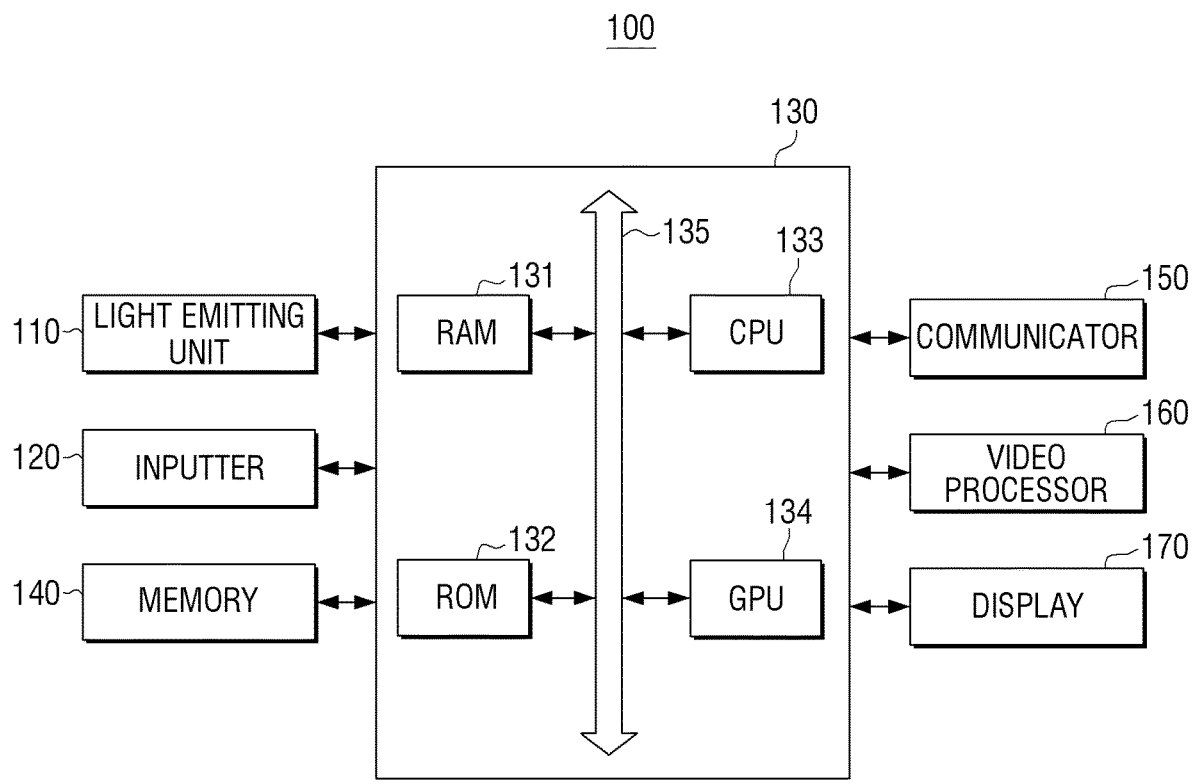
FIG. 3 is a block diagram to illustrate a configuration of the electronic device of FIG. 2 in greater detail.

FIG. 3 is a block diagram to illustrate a configuration of the electronic device of FIG. 2 in greater detail.

Referring to FIG. 3, the electronic device 100 may include the light emitting unit 110, the inputter 120, a processor 130, a memory 140, a communication unit 150, a video processor 160, and a display 170. Here, some operations of the light emitting unit 110, the inputter 120, and the processor 130 are the same as those shown in FIG. 1, and redundant descriptions are omitted.

The processor 130 may include a RAM 131, a ROM 132, a CPU 133, a Graphic Processing Unit (GPU) 134, and a bus 135. The RAM 131, the ROM 132, the CPU 133, the Graphic Processing Unit (GPU) 134, and the like may be connected to each other via the bus 135.

The CPU 133 accesses the memory 140 and performs booting using the O/S stored in the memory 140. Then, the CPU performs various operations using various programs, contents, data, etc. stored in the memory 140.

The ROM 132 stores a command set for booting the system. When the turn-on command is input and power is supplied, the CPU 133 copies the O/S stored in the memory 180 to the RAM 131 according to the instruction stored in the ROM 132, executes O/S to boot the system. When the booting is completed, the CPU 133 copies various programs stored in the memory 140 to the RAM 131, executes the program copied to the RAM 131, and performs various operations.

The GPU 134 displays the UI on the display 170 when the booting of the electronic device 100 is completed. Specifically, the GPU 134 can generate a screen including various objects such as an icon, an image, and a text using an operation unit (not shown) and a rendering unit (not shown). The operation unit calculates attribute values such as coordinate values, shapes, sizes, and colors to be displayed by the respective objects according to the layout of the screen. The rendering unit generates screens of various layouts including the objects based on the attribute values calculated by the operation unit. The screen (or user interface window) generated by the rendering unit is provided to a display, and is displayed in the main display area and the sub display area, respectively. In the above description, the image processing operation according to the present disclosure is performed by the GPU 134. However, in actual implementation, the image processing operation can be performed by the CPU 133 or the GPU 134.

The memory 140 may be implemented as a storage medium in the electronic device 100 and an external storage medium, for example, a removable disk including a USB memory, a web server through a network, and the like. To be specific, the memory 140 may include a hard disk, an SSD, a memory card, a ROM, a USB memory.

Specifically, the memory 140 may store the coordinates of the reflected points extracted using the plurality of images input through the inputter 120. Here, the coordinates of the stored reflection points can be used for the user's gaze detection. The coordinates of the reflected points to be stored may be coordinates excluding the coordinates of the reflection points at the same position included in the plurality of images among the plurality of reflection points extracted from the plurality of images.

The processor 130, using the first image photographed at the time of irradiating light of the first pattern and the second image photographed at the time of irradiating light of the second pattern, from among the plurality of input images, may store coordinates of reflection points extracted to use for detection of the user's gaze in the memory 140. The processor 130, when coordinates of the reflection points to be used for detection of the user's gaze are determined, may control the light emitting unit 110 to irradiate light with the third pattern that is distinguished from the first pattern and the second pattern.

For example, if the first pattern is formed by emitting the first and third light emitting diode among the four light emitting diode and the second pattern is formed by emitting the second and fourth light emitting diode, the third pattern can be formed by making all the four light emitting diode emit light. This is because the external light is removed by using the first pattern and the second pattern, and the pattern necessary for detecting the user's gaze is determined, and after the necessary pattern is determined, the processor 130 may remove the reflection point caused by the external light even if all the light emitting diode are made to emit light.

Specifically, the processor 130 may extract a plurality of reflection points from the third image photographed at the time of irradiating light of the third pattern among the plurality of images input by the inputter 120. Here, the extracted reflection point may include both the reflection point by the light emitting unit 110 and the reflection point by the external lighting.

The processor 130 may then select a reflection point to be used for detecting user's gaze based on the coordinate information of the reflection points stored in the memory 140 among the reflection points extracted from the third image. At this time, the processor 130 can select the reflection point most similar to the coordinate information of the stored reflection point among the reflection points extracted from the third image. Then, the processor 130 can detect the user's gaze using the selected reflection point. That is, a reflection point necessary for user's gaze detection can be detected using a pattern of the reflection points determined in the frame after the pattern of reflection points necessary for user's gaze detection is determined. Accordingly, it is not necessary to generate a difference image, and the memory and time required for detecting the user's gaze are reduced. In the meantime, a method of detecting a reflection point necessary for user's gaze detection using the determined pattern of reflection points will be described in detail with reference to FIGS. 9 and 10.

The communication unit 150 is configured to perform communication with various types of external devices according to various types of communication methods. Specifically, the communication unit 150 can perform communication with an external device such as an external imaging device, an external server, or an external display device.

Specifically, the communication unit 150 may receive a plurality of images from an external device through a wired system such as an antenna, a cable, or a port, or receive a plurality of images through a wireless system such as Wi-Fi and Bluetooth.

The communication unit 150 may transmit information on user's gaze detection that is calculated by the operation of the processor 130 to an external device.

In FIG. 3, the inputter 120 and the communication unit 150 are shown as separate components. However, the electronic device 100 may not include an image capturing unit, or may be configured such that the inputter 120 may include a part or whole of a function of the communication unit 150.

The video processor 160 is a component for processing the content received through the communication unit 150 or the video data included in the content stored in the memory 140 when the display 170 is provided in the electronic device 100. The video processor 160 may perform various image processing such as decoding, scaling, noise filtering, frame rate conversion, resolution conversion, etc. on the video data.

The video processor 160 may then perform image processing on the video data based on the user's gaze detected by the processor 130. Specifically, the video processor 160 may change the area to be displayed on the display 170 among the received images based on the detected user's gaze, or may display a cursor on the received image.

The display 170 can display an image corresponding to the detected gaze of the user. Specifically, if the user is gazing at an image displayed on the display 170, the display 170 may further display a cursor or the like at a position corresponding to the user's gaze of the displayed image. In the meantime, if the user is gazing at the surrounding space, the display 170 may display an image of the peripheral space under the control of the processor 130, and may further display a cursor or the like at a position corresponding to the user's gaze of the displayed image.

Meanwhile, although not shown, the electronic device 100 may further include a sensor such as an illuminance sensor to determine whether the space in which the electronic device 100 is located is indoor or outdoor. At this time, if it is determined that the space in which the electronic device 100 is located is the room according to the sensed illumination value, the processor 130 can emit all of the plurality of light emitting devices constituting the light emitting unit 110. This is because the input image is less likely to include reflection points due to external lighting in the case of the indoor. However, even if it is determined that the electronic device 100 is located indoors, the processor 130 may control the light emitting unit 110 to alternately irradiate light in different patterns.

Figure 4:
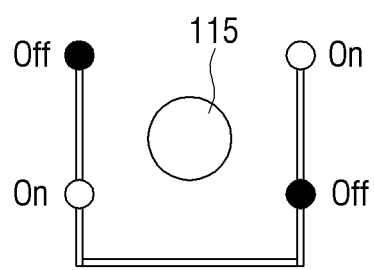
FIG. 4 is a view illustrating an operation of the light emitting unit according to an exemplary embodiment.
Figure 4:
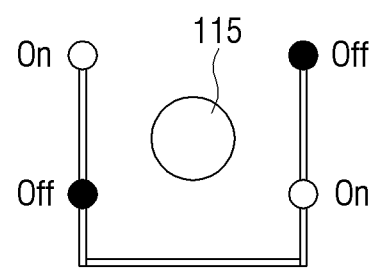

FIG. 4 is a view illustrating an operation of the light emitting unit according to an exemplary embodiment.

The electronic device can control the light emitting unit to alternately irradiate light of different patterns as shown in FIGS. 4A and 4B. Referring to FIG. 4, the light emitting unit may include four light emitting diode. For convenience of description, the light emitting element on the upper left side is numbered 1, the light emitting device on the upper right side is numbered 2, the light emitting element at the lower right end is referred to as 3, and the light emitting element at the lower left end is referred to as 4 in an clockwise direction.

When the electronic device irradiates light in the first pattern according to a preset pattern, the light emitting diode 2 and 4 may emit light, and the light emitting diode 1 and 3 may not emit light, as shown in FIG. 4A. When the light is irradiated with the second pattern, as shown in FIG. 4B, the light emitting diode 1 and 3 may be emitted while the light emitting diode 2 and 4 may not be emitted.

The external lighting may keep emitting light irrelevantly to a pattern of the light emitting unit.

In FIG. 4, a plurality of light emitting diode in a diagonal direction emit light alternately, but in actual implementation, the light emitting devices emit light in the horizontal direction (1, 2/3, 1, 4 are alternately emitted) or in the vertical direction (1, 4/2, and 3 are alternately emitted). In addition, all of the light emitting diode may emit light in the first pattern, and all of the light emitting diode may not emit light in the second pattern.

In FIG. 4, a light emitting unit has four light emitting diode disposed in a quadrangle shape, but the number of light emitting units may be three or less, or four or more. The disposition shape is not limited to quadrangle.

Figure 5:
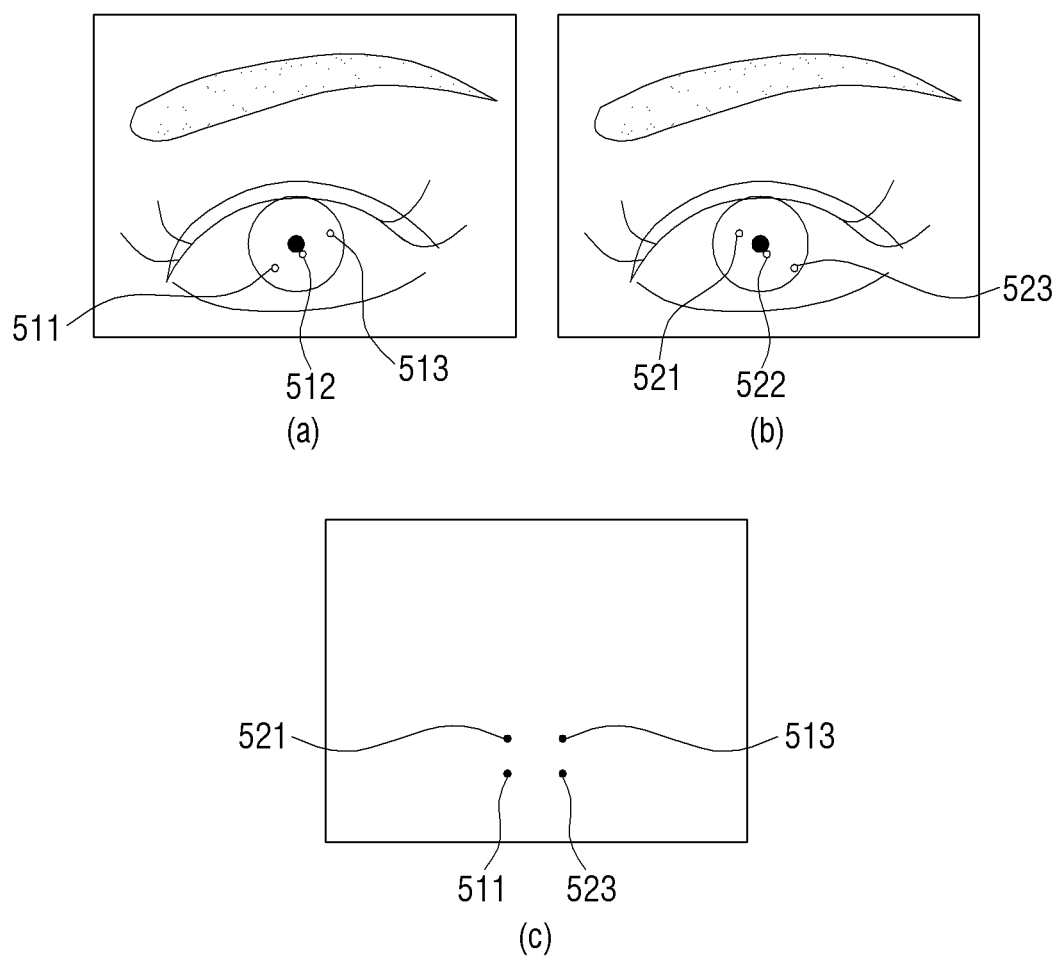
FIG. 5 is a view illustrating a difference image between an image that is photographed according to an operation of the light emitting unit of FIG. 4 and a captured image.

FIG. 5 is a view illustrating a difference image between an image that is photographed according to an operation of the light emitting unit of FIG. 4 and a captured image.

Referring to FIG. 5, FIG. 5A is a first image taken when light is irradiated in the first pattern of FIG. 4A, and FIG. 5B is a second image photographed when light is irradiated in the second pattern of FIG. 4B. In addition, FIG. 5C is a difference image of the first image and the second image. This is based on viewing the light emitting unit and the user in the same direction. When the light emitting unit and the user are viewed in the opposite direction, FIG. 5A is an image taken when light is irradiated in the pattern of FIG. 4B, and FIG. 5B may be a photographed image when light is irradiated in the pattern of FIG. 4A. Hereinafter, for convenience of description, the description will be made with reference to the case of viewing the light emitting unit and the user in the same direction.

Referring to FIG. 5A, the first image may include reflection points 511 and 513 by the light emitting unit and a reflection point 512 by external lighting.

Referring to FIG. 5B, the second image may include the reflection points 521, 523 by the light emitting unit which emits light in the second pattern and the reflection point 522 by external lighting.

Referring to FIG. 5C, the reflection points 511 and 513 of the first pattern and the reflection points 521 and 523 of the second pattern are formed by different light emitting diode, respectively. However, the reflection points 512 and 522 due to the external lighting continue to emit light regardless of the pattern of the external lighting, and may be displayed at the same position as there is no movement of the user between the first image capturing and the second image capturing. Accordingly, the reflection points 512 and 522 due to the external lighting can be removed at the time of generation of the difference image.

Accordingly, the electronic device can extract only the reflection points 511, 513, 521, and 523 due to the light emitting unit from which the reflection points 512 and 522 are removed by the external lighting, and may detect a user's gaze.

Figure 6:
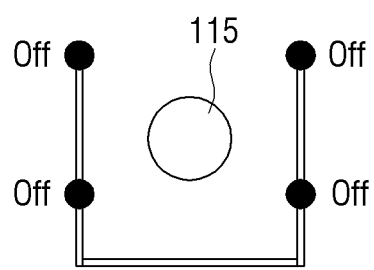
FIG. 6 is a view illustrating an operation of the light emitting unit according to another exemplary embodiment.
Figure 6:
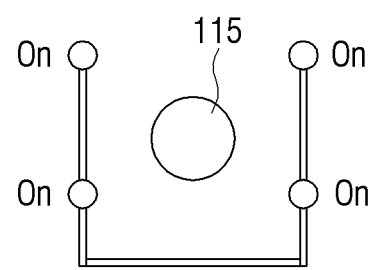

FIG. 6 is a view illustrating an operation of the light emitting unit according to another exemplary embodiment.

The electronic device can control the light emitting unit to alternately irradiate light of different patterns as shown in FIGS. 6A and 6B. Referring to FIG. 6, the light emitting unit may include four light emitting diode. For convenience of description, the upper left light emitting element is 1, the right upper light emitting element is 2, the light emitting element at the lower right end is referred to as 3, and the light emitting element at the lower left end is referred to as 4.

When the electronic device irradiates light in the first pattern according to a preset pattern, the light emitting element may not emit light as shown in FIG. 6A. When the light is irradiated with the second pattern, as shown in FIG. 6B, all the light emitting diode can be emitted.

The external lighting 115 can keep emitting light regardless of a pattern of the light emitting unit.

Figure 7:
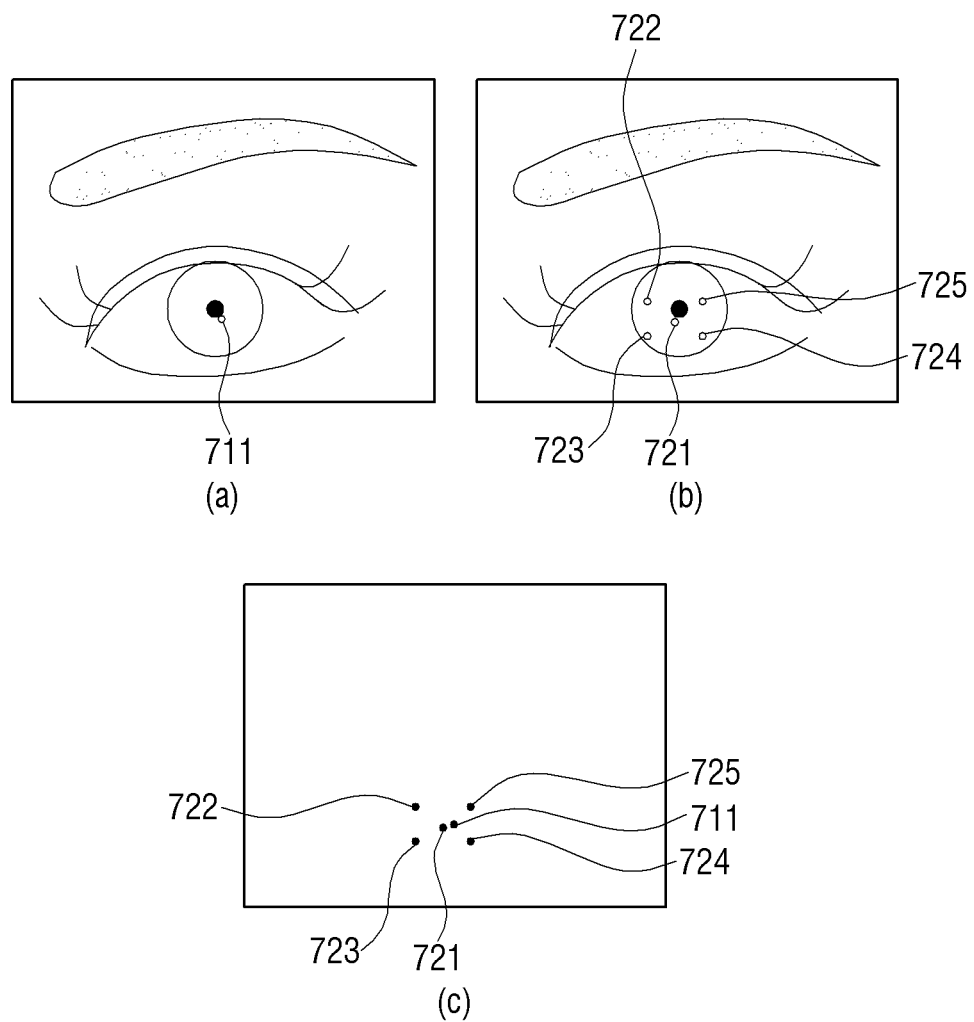
FIG. 7 is a view illustrating a difference image of an image that is captured according to an operation of the light emitting unit of FIG. 6 and the captured image.

FIG. 7 is a view illustrating a difference image of an image that is captured according to an operation of the light emitting unit of FIG. 6 and the captured image.

Referring to FIG. 7, FIG. 7A is a first image taken when light is irradiated in the first pattern of FIG. 6A, FIG. 7B is a first image taken when light is irradiated in the second pattern of FIG. 6B. In addition, FIG. 7C is a difference image of the first image and the second image. At this time, it is assumed that the user's positional shift has occurred between the first image capturing and the second image capturing.

Referring to FIG. 7A, the first image has no light emitting element which emits light according to the first pattern and thus may include only the reflection point 711 by external lighting.

Referring to FIG. 7B, in the second image, since all of the light emitting diode emit light according to the second pattern, the reflection points 722, 723, 724, and 725 by the light emitting unit and the reflection points 721 by external lighting can be included.

At this time, since the position of the user is shifted between the first image capturing and the second image capturing, even if the external lighting emits light at the same position, the position of the reflection point 711 due to external lighting in the first image, and the position of the reflection point 721 due to the external lighting in the second image may be different.

Referring to FIG. 7C, in the difference image of the first image and the second image, the reflection point 711 displayed in the first image and the reflection points 721-725 displayed in the second image can be displayed.

As described above, when the position of the user is moved, the reflection point due to the external lighting cannot be removed only by generating the difference image, so that the electronic device can perform correction for the movement of the user. This will be described below with reference to FIG. 8.

Figure 8:
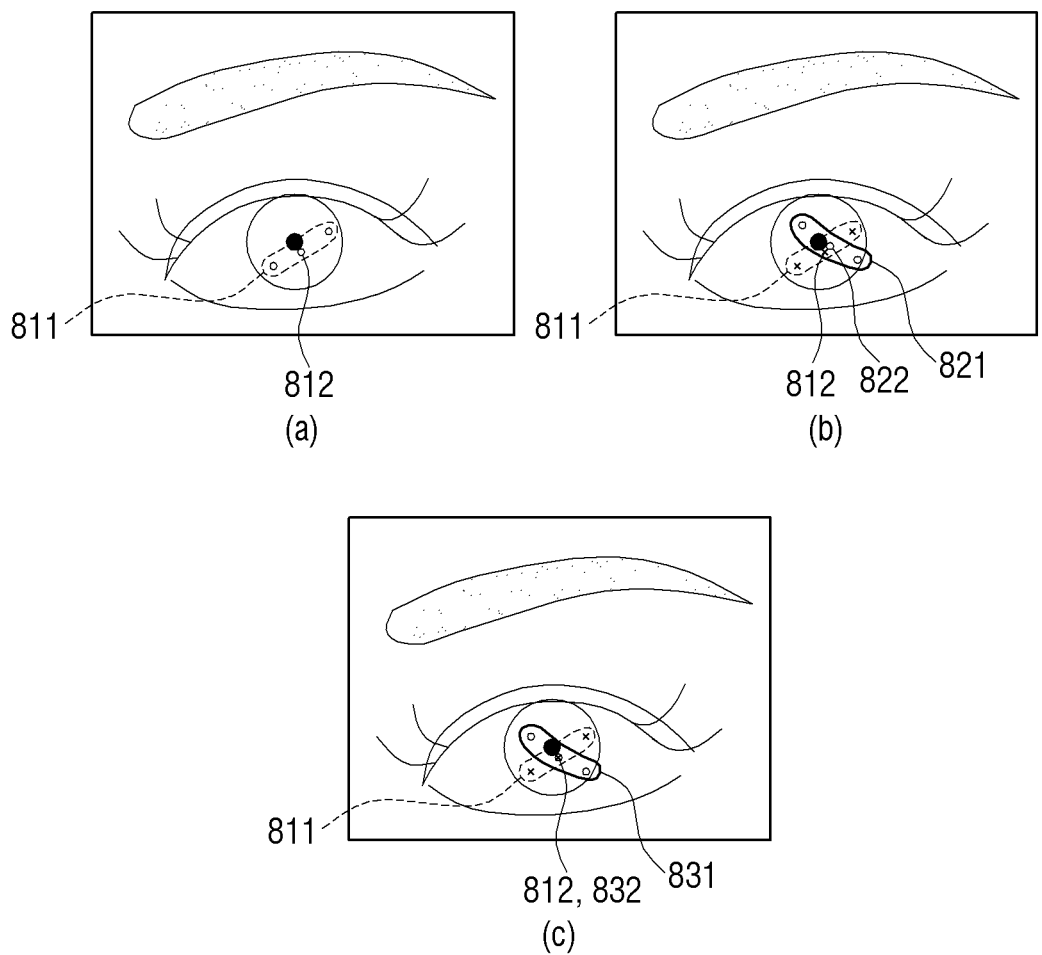
FIG. 8 is a view to describe a method of compensating a movement according to an exemplary embodiment.

FIG. 8 is a view to describe a method of compensating a movement according to an exemplary embodiment. Hereinbelow, for convenience of description, an image captured according to a pattern of the light emitting unit as illustrated in FIG. 4 will be used as a reference.

Referring to FIG. 8, FIG. 8A is an image including a first pattern of FIG. 4A and a reflection point displayed when light is irradiated by external lighting, FIG. 8B further illustrates reflection points in a case when light is irradiated by external light along with the second pattern of FIG. 4B in addition to FIG. 8A. At this time, it is assumed that the user has moved between the first image capturing and the second image capturing. FIG. 8C is an image in which the movement of the user is corrected. On the other hand, this is based on viewing the light emitting portion and the user in the same direction, and in the case where the light emitting portion and the user are viewed in the opposite direction, FIG. 8A can be a photographed image when light is irradiated in the pattern of FIG. 4B. Hereinafter, for convenience of description, the description will be made with reference to the case of viewing the light emitting portion and the user in the same direction.

Referring to FIG. 8A, the first image includes a plurality of reflection points 811 that are generated when light of the first pattern is irradiated outdoor, and the plurality of reflection points 811 may include the reflection point 812 by external lighting.

Referring to FIG. 8B, the second image includes a plurality of reflection points 821 that are generated when light of a second pattern is emitted outdoors, and the plurality of reflection points 821 include reflection points 822 by the external lighting. A plurality of reflection points 811 corresponding to the first pattern shown in FIG. 8B are shown for describing the movement of the user, and are not reflection points displayed in the actual image.

Here, since the position of the user is shifted between the first image capturing and the second image capturing, even if the external lighting is emitted at the same position, the position of the reflection point 812 by the external lighting in the first image may be different from the position of the reflection point 822 due to the external lighting in the two images.

The electronic device may extract the feature point that is distinguished from the reflection point included in the eye area of the user in the first image captured at the time of irradiating the light of the first pattern and the second image captured at the time of irradiating the light of the second pattern and correct the position movement. For example, it may be a starting point or a tail point of the user's eye, or a point area included in an area other than the eye area among the user's face area, which is a characteristic that the structure does not change even if the position of the user's face moves. Here, if only the position of the face of the user is moved and the position of the eye is not moved, the processor 130 may extract the center point of the pupil as a feature point.

Specifically, the electronic device can calculate the positional movement of the user using the extracted feature points on each image, and correct the position of the second image based on the calculated value.

Accordingly, as shown in FIG. 8C, the positions of the reflection points 812 and 832 by the external lighting can be matched through the correction. Then, the electronic device can detect the user's gaze using the reflection point excluding the reflection points 812 and 832 due to external lighting among the plurality of reflection points 811 and 831 by using the position coordinates of the corrected reflection point.

Figure 9:
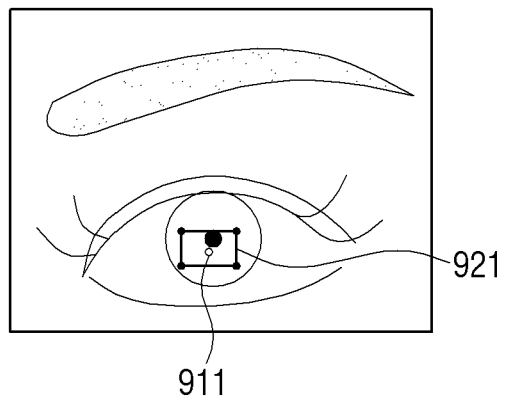
FIG. 9 is a view illustrating a result that is deducted according to an exemplary embodiment.

FIG. 9 is a view illustrating a result that is deducted according to an exemplary embodiment.

The electronic device can distinguish the reflection points of the external lighting and the reflection points of the light emitting unit among a plurality of reflection points included in the image of the user's eye area through the above-described process. In addition, the electronic device can store information about the reflection point by the light emitting unit. Here, the stored information may be the coordinate information of the reflection point by the light emitting unit.

Referring to FIG. 9, the image which captures the eye area displays a plurality of reflection points including the reflection point 911 by the external lighting and the reflection point 921 by the light emitting unit. Here, the reflection point 921 by the light emitting unit may be in a rectangular shape.

Figure 10:
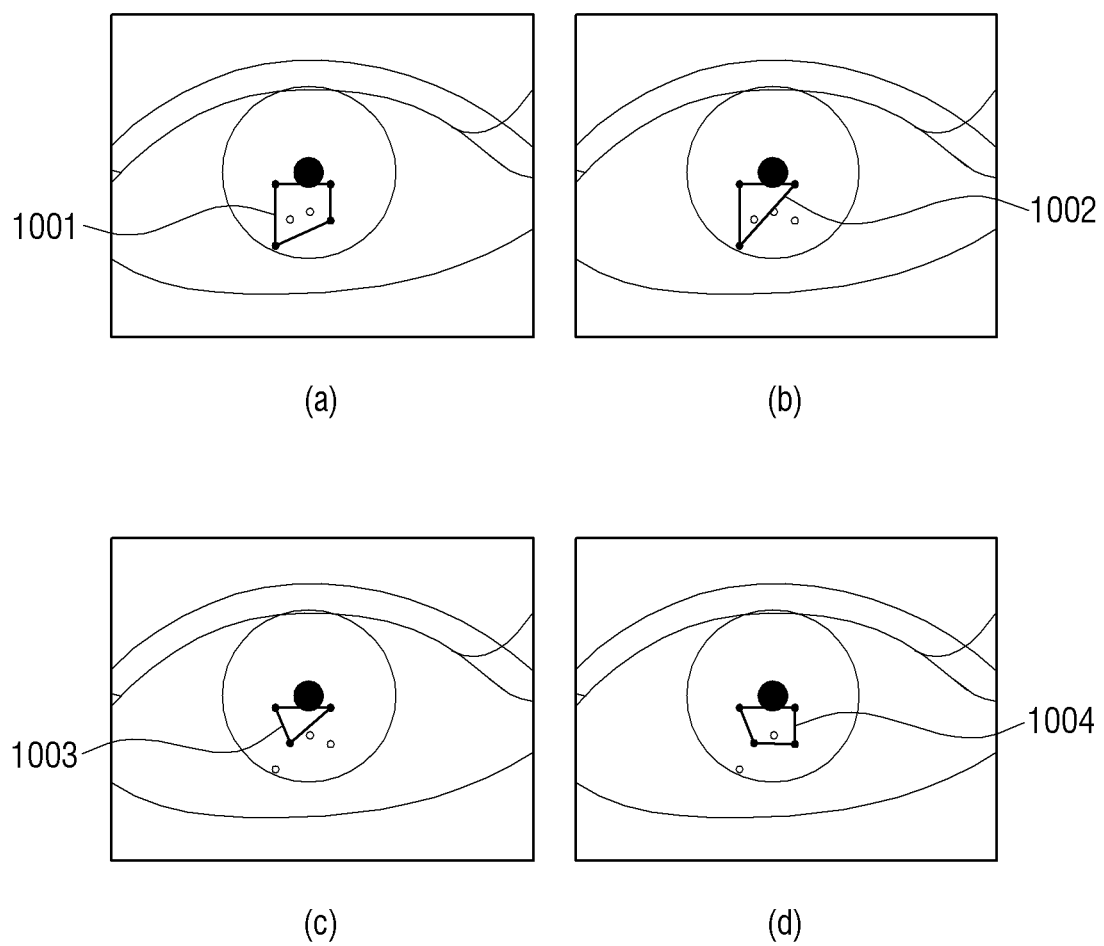
FIG. 10 is a view to describe a method of detecting feature points from an image which is input thereafter, based on a result illustrated in FIG. 9.

FIG. 10 is a view to describe a method of detecting feature points from an image which is input thereafter, based on a result illustrated in FIG. 9.

The electronic device can control the light emitting unit to emit a plurality of light emitting diode without a pattern by dividing the reflection point by the light emitting unit and storing the coordinate information of the reflection point by the light emitting unit. This is because it is possible to eliminate the reflection points for the external lighting even if the light is not irradiated according to the pattern using the stored coordinate information.

Specifically, the electronic device can receive a plurality of mages of the eye area of the user while emitting a plurality of light emitting diode, and extract a plurality of reflection points from the received image. Then, the electronic device can compare the various candidates and the stored coordinate information at the extracted plurality of reflection points, and select the reflection points included in the candidate most similar to the stored coordinate information. The electronic device can then detect the user's gaze using the selected reflection point.

Here, the electronic device can select a reflection point having a position closest to the coordinate information of the stored plurality of reflection points, or a reflection point having the most similar shape when the candidate reflection points are connected. When selecting a reflection point with a similar connection shape, the electronic device may take into account the distance and angle when connecting with the adjacent reflection point.

Referring to FIGS. 10A to 10D, the electronic device may compare various candidates 1001, 1002, 1003, and 1004 from among a plurality of reflection points and stored coordinate information on the reflection point illustrated in FIG. 9 and may select the reflection point included in the candidate 1004 which is most similar to the stored coordinate information.

FIG. 11 is a flowchart to describe a method of detecting a user's gaze according to an exemplary embodiment.

Referring to FIG. 11, first, the electronic device can alternately search for the eyes having the preset pattern in the eye region of the user in step S1110. Specifically, the electronic device can irradiate light by controlling the light emitting unit including a plurality of light emitting diode. Here, the preset pattern includes a plurality of patterns, and each pattern may be formed of light emitted from different light emitting diode among the plurality of light emitting diode.

The electronic device can receive a plurality of images of the user's eye area in step S1120. Specifically, the electronic device can capture an eye area of a user using the provided image capturing unit, or receive an image photographed by an external device. Here, when the electronic device is provided with the image capturing unit, the image capturing unit may be a general camera which photographs at a speed of 30 frames to 60 frames per second.

Then, the electronic device can extract the reflection points of each of the first image and the second image in step S1130. Specifically, the electronic device may extract a reflection point of each of the photographed second images when light of the first pattern and the second pattern are irradiated when light of the first pattern among the plurality of input images is irradiated. Here, the first image and the second image may be consecutive frames.

Then, the electronic device can detect the user's gaze using the remaining reflection points except for the reflection points at the same position among the reflection points extracted from the respective images in step S1140. Specifically, the electronic device can remove the reflection points at the same position using the difference image of the first image and the second image. If there is a movement of the user between the first image capturing and the second image capturing, the electronic device can correct the image according to the movement of the position and then detect the user's gaze using the reflection point.

As described above, by using two images which include reflection points on light of different patterns, a pattern of a light emitting unit can be grasped without prior information on the pattern of the light emitting unit, and even in outdoor environment, a reflection point for detecting a user's gaze correctly can be detected using a low-cost general camera.

Meanwhile, the various embodiments described above can be implemented in a recording medium that can be read by a computer or similar device using software, hardware, or a combination thereof. In accordance with a hardware implementation, the embodiments described in this disclosure may be implemented in the fields of application specific integrated circuits (ASICs), digital signal processors (DSPs), digital signal processing devices (DSPDs), programmable logic devices (PLDs) field programmable gate arrays (FPGAs), processors, controllers, micro-controllers, microprocessors, and an electrical unit for performing other functions. In some cases, embodiments described herein may be implemented by processor 130 itself. According to a software implementation, embodiments such as the procedures and functions described herein may be implemented in separate software modules. Each of the software modules may perform one or more of the functions and operations described herein.

A controlling method of the electronic device according to various exemplary embodiments of the aforementioned present disclosure can be stored in a non-transitory readable medium. The non-transitory readable medium can be mounted in various devices and used.

The non-transitory computer readable medium refers to a medium that stores data semi-permanently, and is readable by an apparatus. Specifically, the above-described various applications or programs may be stored in the non-transitory computer readable medium such as a compact disc (CD), a digital versatile disk (DVD), a hard disk, a Blu-ray disk, a universal serial bus (USB), a memory card, a ROM or etc., and may be provided.

The foregoing example embodiments and advantages are merely examples and are not to be construed as limiting. The present teaching can be readily applied to other types of apparatuses. Also, the description of the example embodiments is intended to be illustrative, and not to limit the scope of the claims, and many alternatives, modifications, and variations will be apparent to those skilled in the art.

What is claimed is:

1. An electronic device comprising:
   a light emitting unit configured to alternately emit light having a preset pattern to an eye area of a user;
   an inputter configured to receive a plurality of images which capture the eye area of the user;
   a memory configured to store coordinate information on remaining reflection points excluding reflection points at a same position, from among extracted reflection points; and
   a processor configured to:
   obtain a first image that is captured at a time of irradiating a first pattern and a second image that is captured at a time of irradiating a second pattern,
   extract reflection points of each of the first image and the second image,
   detect a user's gaze by using remaining reflection points excluding reflection points at a same position from among the extracted reflection points,
   detect the user's gaze by extracting a plurality of reflection points from a third image that is captured at a time of irradiating of a third pattern, from among the plurality of images, and
   use a reflection point selected based on the stored coordinate information from among the extracted plurality of reflection points.

2. The electronic device of claim 1, wherein the processor is further configured to:
   generate a difference image on the first image and the second image,
   extract a reflection point from the difference image, and
   detect the user's gaze using the reflection point that is extracted from the difference image.

3. The electronic device of claim 1, wherein the processor is further configured to:
   extract feature points respectively from the first image and the second image, and
   if positions of the extracted feature points are different, correct the second image so that the position of the feature point extracted from the second image is the same as the position of the feature point extracted from the first image.

4. The electronic device of claim 3, wherein the processor, while the position of the feature point of the first image and the position of the feature point of the second image are coincided, is further configured to:
   extract a center point of a pupil in the eye area of the user from each of the first image and the second image, and
   if the positions of the extracted center points of the pupil are different, correct the second image to be coincided with the position of the extracted center point of the pupil of the first image.

5. The electronic device of claim 1, wherein the inputter captures the eye area of the user at speed of 30 to 60 frames per second.

6. The electronic device of claim 1,
wherein the light emitting unit comprises a plurality of light emitting diodes which are spaced apart from each other, and
wherein the processor controls the plurality of light emitting diodes so that different light emitting diodes emit light according to the first pattern and the second pattern.

7. The electronic device of claim 6, wherein the processor is further configured to control the plurality of light emitting diodes so that all the plurality of light emitting diodes emit light according to the first pattern, and all the plurality of light emitting diodes do not emit light according to the second pattern.

8. The electronic device of claim 1,
wherein the light emitting unit comprises a plurality of light emitting diodes which are spaced apart from each other, and
wherein the processor is further configured to control the plurality of light emitting diodes so that all the plurality of light emitting diodes emit light according to the third pattern.

9. A controlling method of an electronic device, the method comprising:
alternately emitting light having a preset pattern to an eye area of a user;
obtaining a first image that is captured the eye area at a time of irradiating a first pattern and a second image that is captured the eye area at a time of irradiating a second pattern;
extracting reflection points of each of a first image and a second image;
detecting a user's gaze by using remaining reflection points excluding reflection points at a same position from among the extracted reflection points;
storing coordinate information on remaining reflection points excluding reflection points at a same position, from among the extracted reflection points;
extracting a plurality of reflection points from a third image that is captured at a time of irradiating of a third pattern from among a plurality of images; and
detecting the user's gaze using reflection points that are selected based on the stored coordinate information from among the extracted plurality of reflection points.

10. The method of claim 9, wherein the detecting of the user's gaze comprises:
generating a difference image on the first image and the second image,
extracting a reflection point from the difference image, and
detecting the user's gaze using the reflection point that is extracted from the difference image.

11. The method of claim 9, further comprising:
extracting feature points respectively from the first image and the second image; and
if positions of the extracted feature points are different, correcting the second image so that the position of the feature point extracted from the second image is the same as the position of the feature point extracted from the first image.

12. The method of claim 11, further comprising:
while the position of the feature point of the first image and the position of the feature point of the second image are coincided, extracting a center point of a pupil in the eye area of the user from each of the first image and the second image; and
if the positions of the extracted center points of the pupil are different, correcting the second image to be coincided with the position of the extracted center point of the pupil of the first image.

13. The method of claim 9, further comprising capturing the eye area of the user at speed of 30 to 60 frames per second.

14. The method of claim 9, wherein the emitting of light comprises emitting different light emitting diodes from among a plurality of light emitting diodes which are spaced apart from each other according to the first pattern and the second pattern.

15. The method of claim 14, wherein the emitting of light comprises:
emitting the plurality of light emitting diodes according to the first pattern, and
not emitting the plurality of light emitting diodes according to the second pattern.

16. The method of claim 9, the emitting of light comprises emitting all the plurality of light emitting diodes that are spaced apart from each other according to the first pattern and the second pattern.

17. A computer readable recording medium including a program for executing a control method of an electronic device, wherein the control method comprises:
alternately emitting light having a preset pattern to an eye area of a user;
obtaining a first image that is captured the eye area at a time of irradiating a first pattern and a second image that is captured the eye area at a time of irradiating a second pattern;
extracting reflection points of each of a first image and a second image;
detecting a user's gaze by using remaining reflection points excluding reflection points at a same position from among the extracted reflection points;
storing coordinate information on remaining reflection points excluding reflection points at a same position, from among the extracted reflection points;
extracting a plurality of reflection points from a third image that is captured at a time of irradiating of a third pattern from among a plurality of images; and
detecting the user's gaze using reflection points that are selected based on the stored coordinate information from among the extracted plurality of reflection points.

* * * * *